United States Patent
Asikainen et al.

(10) Patent No.: US 9,969,669 B2
(45) Date of Patent: May 15, 2018

(54) METHOD FOR PRODUCING MUCONIC ACIDS AND FURANS FROM ALDARIC ACIDS

(71) Applicant: Teknologian tutkimuskeskus VTT Oy, Espoo (FI)

(72) Inventors: Martta Asikainen, Espoo (FI); David Thomas, Espoo (FI); Ali Harlin, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days. days.

(21) Appl. No.: 15/317,983

(22) PCT Filed: Jun. 15, 2015

(86) PCT No.: PCT/FI2015/050432
§ 371 (c)(1),
(2) Date: Dec. 12, 2016

(87) PCT Pub. No.: WO2015/189481
PCT Pub. Date: Dec. 17, 2015

(65) Prior Publication Data
US 2017/0137363 A1   May 18, 2017

(30) Foreign Application Priority Data

Jun. 13, 2014 (FI) ...................................... 20145554

(51) Int. Cl.
| | | |
|---|---|---|
| *C07C 67/08* | (2006.01) | |
| *C07C 51/377* | (2006.01) | |
| *C07D 307/68* | (2006.01) | |
| *B01J 23/34* | (2006.01) | |

(52) U.S. Cl.
CPC ............. *C07C 51/377* (2013.01); *B01J 23/34* (2013.01); *C07C 67/08* (2013.01); *C07D 307/68* (2013.01)

(58) Field of Classification Search
CPC ................................ C07C 55/14; C07C 67/08
See application file for complete search history.

(56) References Cited

FOREIGN PATENT DOCUMENTS

| | | | |
|---|---|---|---|
| FR | 2723945 A1 | 3/1996 | |
| FR | 2723946 A1 | 3/1996 | |
| JP | 2008127282 A | 6/2008 | |
| WO | WO2010144862 A2 | 12/2010 | |
| WO | WO2014032731 A1 | 3/2014 | |
| WO | WO2015084265 A1 | 6/2015 | |

OTHER PUBLICATIONS

Ackman, R.G. et al: The condensation of methyl ketones with furan. Departments of Chemistry—Ontario Agricultural College and University of Toronto. Sep. 1955. vol. 20. pp. 1147-1158.

Ahmad, I. et al: Sulfite-Driven, Oxorhenium-Catalyzed Deoxydehydration of Glycols. Organometallics. 2011. vol. 30. pp. 2810-2818.

Costigan, M.G. et al: Synthesis and Physicochemical Properties of the Furan Dicarboxylic Acid, 3-Carboxy-4-methyl-5-propyl-2-furanpropanoic Acid, an Inhibitor of Plasma Protein Binding in Uraemia. J. Pharm. Pharmacol. 1996. vol. 48. pp. 635-640.

Haworth, W.N. et al: 1. The Conversion of Sucrose into Furan Compounds. 2. 5-Disubstituted Tetrahydrofurans and their Products of Ring Scission. Journal of the Chemical Society. Sep. 12, 1944. pp. 1-4.

Lewkowski, J. et al: Convenient Synthesis of Furan-2,5-dicarboxylic Acid and its Derivatives. Polish Journal of Chemistry. 2001. vol. 75, No. 12. pp. 1943-1946.

Li, X. et al: Highly efficient chemical process to convert mucic acid into adipic acid and DFT studies of the mechanism of the rhenium-catalyzed deoxydehydration. Angew. Chem. Int. Ed. 2014. vol. 53. pp. 4200-4204.

Shiramizu, M. et al: Deoxygenation of Biomass-Derived Feedstocks: Oxorhenium-Catalyzed Deoxydehydration of Sugars and Sugar Alcohols. Angew. Chem. Int. Ed. 2012. vol. 51. pp. 1-6.

Shiramizu, M. et al: Expanding the scope of biomass-derived chemicals through tandem reactions based oxorhenium-catalyzed deoxydehydration. Angew. Chem. Int. Ed. 2013. vol. 52. pp. 12905-12909.

Taguchi, Y. et al: One-step Synthesis of Dibutyl Furandicarboxylates from Galactaric Acid. Chemistry Letters. 2008. vol. 37. pp. 50-51.

*Primary Examiner* — Gregory Listvoyb

(74) *Attorney, Agent, or Firm* — Seppo Laine Oy

(57) ABSTRACT

The present invention relates to selective catalytic dehydroxylation method of aldaric acids for producing muconic acid and furan chemicals, which can be used directly in fine chemical and polymer applications (FCA/FDCA) and as intermediates in the preparation of industrially significant chemicals, such as terephthalic acid, adipic acid, caprolactone, caprolactam, nylon 6.6, 1,6-hexanediol and multiple pharmaceutical building blocks (MA/MAME).

17 Claims, 1 Drawing Sheet

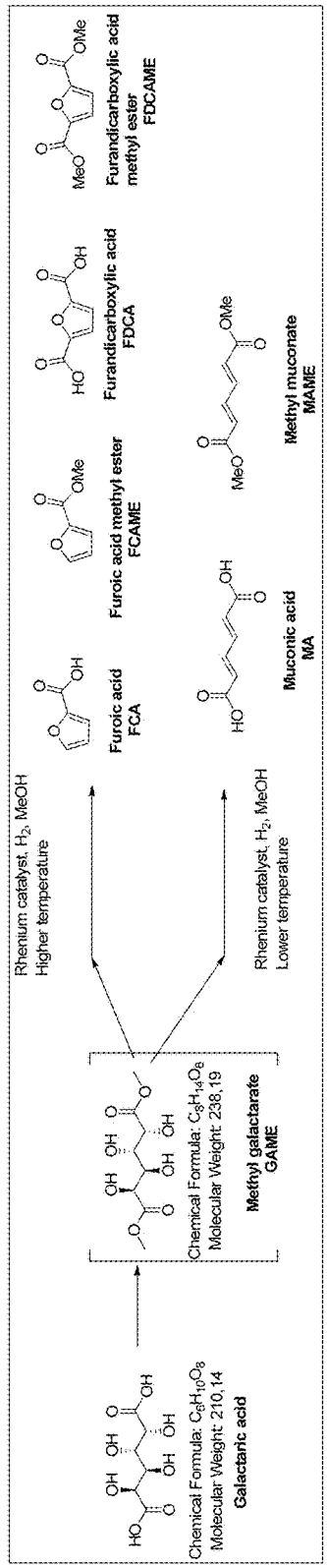

METHOD FOR PRODUCING MUCONIC ACIDS AND FURANS FROM ALDARIC ACIDS

FIELD

The present invention relates to the production of sugar acid platform chemicals from aldaric acid(s) via selective catalytic dehydroxylation. In particular, the present invention relates to the production of muconic acid(s) and furan(s) which are important intermediates in the production of wide variety of industrially significant chemicals and pharmaceutical building blocks.

BACKGROUND

Cellulosic biomass has recently attracted much attention as a renewable feedstock for chemicals and fuels. The industrially relevant compounds are typically produced via crude oil derived processes or by employing biotechnical approaches such as fermentation. One major challenge in the field is that the bio compounds are typically too oxygen-rich to be compatible with the current petroleum-based industry. The search for efficient deoxygenation methods has resulted a growing interest towards catalytic deoxydehydration (DODH) methods, in order to selectively convert bio-based resources into target chemicals.

In the prior art, Rennovia (WO 2010/144862 A2) describes a process for converting glucose to an adipic acid product via catalytic oxidation (glucose into glucaric acid) and catalytic hydrodeoxygenation (glucaric acid into adipic acid) by using hydrodeoxygenation catalyst together with a halogen source and $H_2$.

Shiramizu and Toste (2013) describe a moderate conversion (43-94%) of mucic acid into adipic acid ester by using DODH and hydrogenation reaction. One of the downsides on muconic acid production according to Shiramizu and Toste is a remarkable stoichiometric sacrifice of the used 3-pentanol or 1-butanol (2-4 moles of alcohol spent per one mole of muconic acid product). Thus, one of the downsides on muconic acid production is a remarkable stoichiometric sacrifice of the used 3-pentanol or 1-butanol. For synthesis of muconic acid high temperatures are used (155° C.). Also the method uses fossil pentanol instead of renewable alcohol, such as methanol. In addition, pentanol as a reductant gives 4 molar equivalents of oxidized pentanol as a by-product.

Li et al. (2014) describe even more efficient conversion (up to 99%) of mucic acid into muconic acid through a DODH reaction, which is catalyzed by an oxorhenium complex. By combining DODH with transfer-hydrogenation reaction, mucic acid can be successfully converted into adipic acid. Li et al. use fossil pentanol and also an acid in addition to catalyst in their reactions. Shiramizu & Toste and Li et al. both describe the use of methyltrioxorhenium as a catalyst and 3-pentanol (or 1-butanol) as reductants, with reaction temperatures varying from 120° C. to 170° C.

Furan chemicals may also be produced via dehydroxylation of aldaric acids. However, current methods use strong mineral acids as reagents and reaction times are long, up to 40 hours (FR2723945, Taguchi et al., 2008).

Ahmad et al. (2011) describe production of olefins via sulfite-driven oxorhenium-catalyzed deoxydehydration of glycols. Solid reductant is used, which produces solid waste materials. Hydrogen is mentioned as an economically viable reductant, but this is only shown with THF. Ahmad et al. does not describe a method able to produce furans or muconic acids by using the same process set-up and only varying temperature.

As known, crude oil is a finite resource but essential. On the other hand, aldaric acids, such as galactric acid, can be produced from pectin and other non-edible carbohydrates. By converting aldaric acids to muconic acid and/or furans, a doorway is opened which allows for a wide variety of compounds to be prepared from bio-based resources, which would otherwise be prepared from crude oil stock. Thus, there is a need for a green method that avoids the use of finite resources and instead uses the advantageous techniques, utilizing organic synthesis and catalyst tools and allowing easy scalability, selectivity and ready purification of the desired chemicals.

SUMMARY OF THE INVENTION

It is an object of the present invention to produce muconic acids and furan chemicals from aldaric acids by an environmentally benign method.

Furthermore, the present invention describes a selective method for converting aldaric acids, such as galactaric acid and glucaric acid, to muconic acids and furans by the use of organic synthesis and catalysis tools, in particular a catalytic dehydroxylation.

More precisely, the method of the present invention is characterized by what is disclosed in the characterizing part of claim 1. Uses of the present invention are characterized in claims 17 and 18.

Advantages of the present invention comprise utilizing non-edible carbohydrates into intermediates, which can be used in the production of industrially important chemicals and pharmaceutical building blocks. In addition, the method described herein allows easy scalability and purification of the obtained products.

Another advantage is that the method is green and results low energy consumption (based on e.g. reaction temperatures and times) and low waste production (based on e.g. $H_2$ reductant).

Next, the present technology is described more closely with reference to certain embodiments.

BRIEF DESCRIPTION OF THE DRAWING

FIG. 1 describes the two temperature controlled routes from galactaric acid to muconic acid and furans via rhenium catalyzed dehydroxylation reactions.

EMBODIMENTS

The present invention relates to the production of sugar acid platform chemicals, more precisely muconic acid and furans, such as furoic acid and furandicarboxylic acid, from aldaric acid(s) via selective catalytic dehydroxylation.

Aldaric acids are a group of sugar acids, where the terminal hydroxyl groups of the sugars have been replaced by terminal carboxylic acids, and are characterized by the formula $HOOC-(CHOH)_n-COOH$. Nomenclature of the aldaric acids is based on the sugars from which they are derived. For example, glucose is oxidized to glucaric acid, galactose to galactaric acid and xylose to xylaric acid. Unlike their parent sugars, aldaric acids have the same functional group at both ends of their carbon chain. Thus, two different aldaric acids can produce the same muconic acid.

According to one preferred embodiment of the present invention, the method comprises heating the aldaric acid with a solvent and a reductant in a pressurized container to temperatures between 90 to 300° C. in the presence of a transition metal catalyst for a pre-determined reaction time and purifying the resulting product or products.

Particularly, the method comprises a selective catalytic dehydroxylation of aldaric acid(s), wherein the catalysis is selectively directed towards muconic acid by using catalytic temperatures between 90 and 150° C., such as 100 to 120° C. and preferably of about 100° C. On the other hand, said catalysis can be selectively directed towards furans by using catalytic temperatures between 150 and 300° C., such as 150 to 250° C. and preferably of about 200° C. However, all the compounds II to IX are also being produced at temperatures between 120 and 150° C. The reaction temperatures can be selected and adjusted based on targeted products, as e.g. described in the examples below. The reaction typically starts from galactric acid, but other aldaric acids, such as glucaric acid, may also be used.

As previously said, the catalysis of the present invention can be selectively directed towards muconic acid route or furan route by only adjusting the reaction temperature and time. Such surprising and advantageous finding has not been disclosed before in the art.

One important aspect of the invention is to select an efficient and functional combination of catalyst, solvent and reductant. Earlier attempts in the prior art have failed to facilitate the use of light (i.e. short) alcohols, such as methanol, ethanol and n-butanol, for the reduction step. The inventors of the present invention have managed to develop such a combination providing excellent results towards the desired end-products. Thus, an example of such a combination is to use methyl trioxo rhenium catalyst together with a light alcohol such as methanol as a solvent together with hydrogen as a reductant. The products obtained from the muconic acid route, when using galactaric acid as the aldaric acid and such catalyst/reductant/solvent combination as described herein, comprise muconic acid (MA) and methyl muconate (MAME). Consequently, the furan route provides products such as furoic acid (FCA), furoic acid methyl ester (FCAME), furandicarboxylic acid (FDCA) and furandicarboxylic acid methyl ester (FDCAME).

However, other transition metal catalysts besides rhenium, such as molybdenum, vanadium and palladium catalysts, may also be used.

One major advantage of using the above mentioned combination is that the hydrogen results in $H_2O$ as a byproduct, thus leaving only an alcohol solvent, such as methanol, which is easy to wash or distil off in the purification steps. Hydrogen can also be recycled and it is cheaper compared to other prior art reductants, such as 1-butanol. Other reductants than alcohols are also problematic in the purification step and must be physically removed. Thereby the method is particularly green and produces only low amounts of waste.

The method as herein described is also able to be performed at lower temperatures compared to the prior art methods, where the energy consumption remains low. Relating to the previous, the reaction time is set between 1 minute to 70 hours, preferably between 1 to 2 hours and in particular between 1 to 60 minutes, making the method even more energy efficient. However, the reaction time depends on the targeted product. Typically longer times (such as 48 to 70 hours) are necessary for obtaining MA/MAME and shorter times (1 minute to 60 minutes, preferably 1 minute to 10 minutes) are applicable when producing furan products.

The purification of the produced products comprises filtering any solid precipitate, washing the precipitate with alcohol and drying the washed product(s) for example by evaporation. The organic phase having the desired product (s) of the present invention is subsequently evaporated and then purified, for example, by silica column chromatography. The results are confirmed by further analysis methods generally known in the art.

The present invention is illustrated by the following non-limiting examples. It should be understood, however, that the embodiments given in the description above and in the examples are for illustrative purposes only, and that various changes and modifications are possible within the scope of the claims.

EXAMPLES

Numbering and structural formulas of the relevant chemical compounds of the following examples:

Galactaric Acid (I)

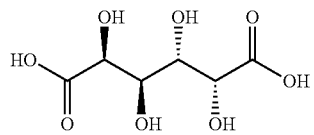

2,4-Hexanedioic Acid (2E, 4E) (II)

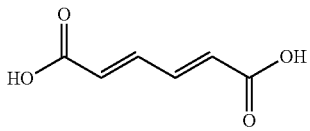

2,4-Hexanedioic Acid 1,6-dimethyl Ester (2E, 4E) (III)

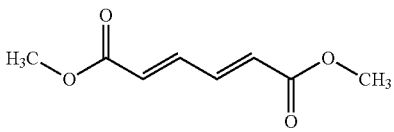

2-Furancarboxylic Acid (IV)

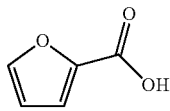

2-Furancarboxylic Acid Methyl Ester (V)

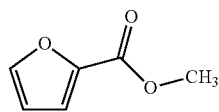

2,5-Furandicarboxylic Acid (VI)

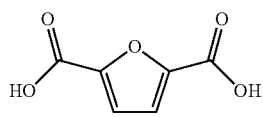

2,5-Furandicarboxylic Acid 2,5-dimethyl Ester (VII)

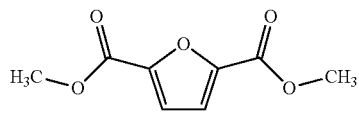

2,4-Hexanedioic Acid 1,6-diethyl Ester (2E, 4E) (VIII)

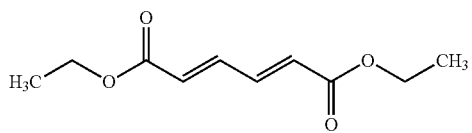

2,4-Hexanedioic Acid 1,6-dibutyl Ester (2E, 4E) (IX)

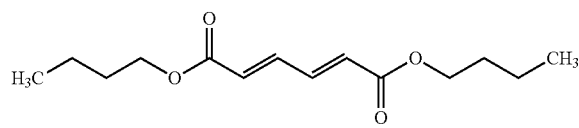

General Method

Reactions were conducted in 25 ml Teflon coated pressure vessels. Product yields were determined using GC-FID with external calibration for each product compound. Standard esterification methods of the corresponding carboxylic acids were used to produce the ester standards for the calibrations. The results were confirmed using GC-MS and NMR analyses.

Example 1 Catalytic Dehydroxylation of Galactaric Acid (I) for the Production of Compounds II-VII Galactaric acid (1.0 g, 4.76 mmol), methyl trioxo rhenium (0.12 g, 0.47 mmol, 10 mol %) and methanol (10 ml) were charged in the reaction vessel. The reaction vessel was pressurised with hydrogen and heated up to the reaction temperature (Table 1). After the indicated reaction time the mixture was cooled down to room temperature, any solid precipitate was filtered, washed with methanol (5 ml) and dried. The solvent fraction was concentrated in a rotary evaporator. Purification was by flash silica column chromatography. The different fractions were analysed with GC-FID, GC-MS and NMR.

TABLE 1

Experiments with galactaric acid with MTO/MeOH

| # | T (° C.) | Gas, (bar) | time (h) | Yield (%) | | | | | |
|---|---|---|---|---|---|---|---|---|---|
| | | | | II | III | IV | V | VI | VII |
| 1 | 100 | $H_2$ (5) | 70 | 0.1 | 10.7 | | | 0.1 | |
| 2 | 100 | $H_2$ (10) | 48 | 0.02 | 6.7 | 0.03 | 0.17 | 0.09 | 0.13 |
| 3 | 120 | $H_2$ (5) | 48 | | 12.3 | | 0.08 | 0.09 | 0.12 |
| 4 | 150 | $H_2$ (5) | 70 | 0.1 | 0.4 | 3.1 | 5.2 | 0.2 | 1.4 |
| 5 | 200 | $H_2$ (5) | 2 | 0.8 | 0.9 | 11.2 | 1.9 | 1.7 | 0.6 |
| 6 | 200 | $H_2$ (5) | 1 | 0.1 | 1.6 | 9.6 | 14.7 | 0.6 | 2.3 |
| 7 | 200 | $H_2$ (5) | 0.25 | 0.87 | 1.4 | 6.09 | 14.0 | 0.88 | 3.6 |

Example 2 Catalytic Dehydroxylation of Galactaric Acid (I) for the Production of Compound VIII Galactaric acid (1.0 g, 4.76 mmol), methyl trioxo rhenium (0.12 g, 0.47 mmol, 10 mol %) and ethanol (10 ml) were charged in the reaction vessel. The reaction vessel was pressurised with hydrogen and heated up to the reaction temperature (Table 2). After the indicated reaction time the mixture was cooled down to room temperature, any solid precipitate was filtered, washed with ethanol (5 ml) and dried. The solvent fraction was concentrated in a rotary evaporator. The different fractions were analysed with GC-FID, and GC-MS.

TABLE 2

Experiments with galactaric acid with MTO/EtOH

| # | T (° C.) | Gas, (bar) | time (h) | Yield (%) VIII |
|---|---|---|---|---|
| 8 | 120 | $H_2$ (5) | 48 | 19.2 |

Example 3 Catalytic Dehydroxylation of Galactaric Acid (I) for the Production of Compound IX Galactaric acid (1.0 g, 4.76 mmol), methyl trioxo rhenium (0.12 g, 0.47 mmol, 10 mol %) and 1-butanol (10 ml) were charged in the reaction vessel. The reaction vessel was pressurised with hydrogen and heated up to the reaction temperature (Table 3). After the indicated reaction time the mixture was cooled down to room temperature, any solid precipitate was filtered, washed with butanol (5 ml) and dried. The solvent fraction was concentrated in a rotary evaporator. The different fractions were analysed with GC-FID, and GC-MS.

TABLE 3

Experiments with galactaric acid with MTO/BuOH

| # | T (° C.) | Gas, (bar) | time (h) | Yield (%) IX |
|---|---|---|---|---|
| 9 | 120 | H$_2$ (5) | 48 | 21.4 |

Example 4 Purification of Mucic Acid Methyl Ester from Reaction #1

After the solvent fraction was concentrated to give a purple powder (528 mg) it was dissolved into acetone (10 g) and then added to silica gel (1 g). This was then evaporated to a powder and eluted from a flash column (11 cm silica gel) with solvent 10% ethyl acetate/90% hexane. Removal of the solvent from the product fractions gave compound III as a white powder, 110.4 mg, 8.2% yield. $^1$H NMR (D6-DMSO) 3.70 (6H, s, CH$_3$), 6.49 (2H, d, J 13.95 alkene H), 7.40 (2H, d, J 13.95, alkene H). $^{13}$C NMR (D6-DMSO) 165, 141, 128, 51. GC-MS m/z 170.

CITATION LIST—PATENT LITERATURE

1. WO 2010/144862 A2
2. FR2723945

CITATION LIST—NON-PATENT LITERATURE

1. Shiramizu, M. and Toste, F. D., 2013, *Expanding the Scope of Biomass-derived Chemicals through Tandem Reactions Based on Oxorhenium-Catalyzed Deoxydehydration*, Angew. Chem. Int., Vol 52, pp. 12905-12909, DOI: 10.1002/anie.201307564.
2. Li, X., Wu, D., Lu, T., Yi, G., Su, H. and Zhang, Y., 2014, *Highly Efficient Chemical Process to Convert Mucic Acid into Adipic Acid and DFT Studies of the Mechanism of the Rhenium-Catalyzed Deoxydehydration*, Angew. Chem., Vol 126, pp. 1-6, DOI: 10/1002/ange.201310991.
3. Taguchi, Y., Oishi, A., Iida, H., 2008, *One-step Synthesis of Dibutyl Furandicarboxylates from Galactaric Acid*, Chem. Lett., Vol 37, pp. 50-51, DOI: 10.1246/cl.2008.50.
4. Ahmad, I., Chapman, G., Nicholas, K. M., 2011, *Sulfite-Driven, Oxorhenium-Catalyzed Dehydroxylation of Glycols*, Organometallics, Vol 30, pp. 2810-2818.

The invention claimed is:

1. A method for producing muconic acid from aldaric acid, wherein the method is also capable of producing furan chemicals, the method comprising selective catalytic dehydroxylation of the aldaric acid by heating the aldaric acid with a solvent and a reductant in a pressurized container to temperatures between 90 to 300° C. in the presence of a transition metal catalyst for a pre-determined reaction time and purifying the resulting product(s), wherein the catalysis is directed towards muconic acid by using catalytic temperatures between 90 and 150° C. and towards furan chemicals by using catalytic temperatures between 150 and 300° C.

2. The method according to claim 1, wherein the aldaric acid is galactaric acid having formula I:

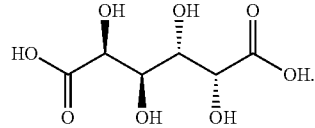

3. The method according to claim 1, wherein the catalysis is selectively directed towards muconic acid by using a catalytic temperature between 100 and 150° C.

4. The method according to claim 1, wherein the catalysis is selectively directed towards furan chemicals by using catalytic temperatures between 150 and 250° C.

5. The method according to claim 1 for producing compounds having structural formulas II, III, VIII and IX by using temperatures between 90 and 150° C.

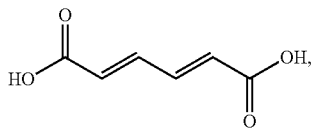

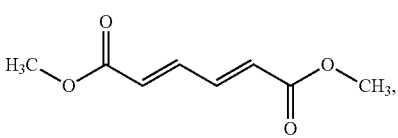

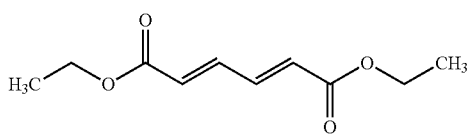

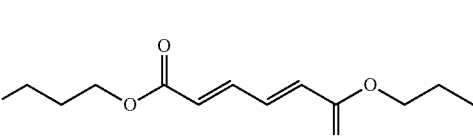

6. The method according to claim 1 for producing compounds having structural formulas IV-VII by using temperatures between 150 and 300° C.

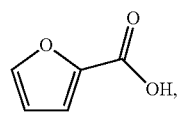

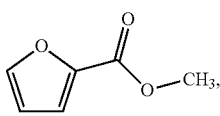

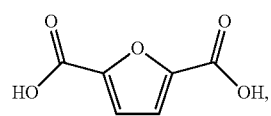

-continued

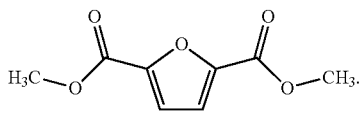
VII

7. The method according to claim 1, wherein the transition metal catalyst is selected from rhenium, palladium, vanadium and molybdenum catalysts.

8. The method according to claim 1, wherein the catalyst is methyl trioxo rhenium.

9. The method according to claim 1, wherein the catalyst is used at a ratio of 1.0 to 10 mol-% per aldaric acid with mucic acid or mucic acid alkyl ester.

10. The method according to claim 1, wherein the reductant is hydrogen.

11. The method according to claim 1, wherein the solvent is selected from methanol, ethanol or butanol.

12. The method according to claim 1, wherein the pressure inside the container is adjusted to a level of 1 to 20 bars with hydrogen gas.

13. The method according to claim 1, wherein the reaction time is 1 minute to 70 hours.

14. The method according to claim 1, wherein the reaction time is 1 to 70 hours when targeting towards MA/MAME and 1 minute to 60 minutes when targeting towards furan chemicals.

15. The method according to claim 1, wherein the purification comprises filtering any solid precipitate, washing the precipitate with alcohol, drying the washed product(s) and subsequently evaporating the organic phase and using a chromatography for recovering the desired products.

16. The method according to claim 1, wherein the transition metal catalyst is selected from rhenium catalysts.

17. The method according to claim 1, wherein the catalysis is selectively directed towards muconic acid by using a catalytic temperature of 120° C.

* * * * *